United States Patent [19]

Wilson et al.

[11] Patent Number: 4,618,103

[45] Date of Patent: Oct. 21, 1986

[54] HOSPITAL WASTE DISPOSAL SYSTEM

[75] Inventors: Joseph H. Wilson; David N. Lasiter, both of Indianapolis; Randall G. McKee, Yorktown, all of Ind.

[73] Assignee: Medical Safetec, Inc., Indianapolis, Ind.

[21] Appl. No.: 541,140

[22] Filed: Oct. 12, 1983

[51] Int. Cl.⁴ ............... B02C 13/09; B02C 9/04; B02C 19/12; F24H 1/00

[52] U.S. Cl. ................... 241/41; 241/186.2; 241/188 R; 241/DIG. 14; 241/99; 220/334

[58] Field of Search ............ 241/33, 38, 41, 99, 241/100, 101.2, 186 R, 186.2, DIG. 14, 188 R; 210/300, 301; 220/87, 334; 239/193, 194

[56] References Cited

U.S. PATENT DOCUMENTS

| | | | |
|---|---|---|---|
| 3,332,629 | 7/1967 | Miller | 241/33 |
| 3,901,349 | 8/1975 | DeNoyer | 241/186 R X |
| 3,926,379 | 12/1975 | Dryden et al. | 241/69 |
| 4,362,628 | 12/1982 | Kennedy et al. | 210/167 X |

FOREIGN PATENT DOCUMENTS

619810  9/1935  Fed. Rep. of Germany .

Primary Examiner—Howard N. Goldberg
Assistant Examiner—Timothy V. Eley
Attorney, Agent, or Firm—Dick and Harris

[57] ABSTRACT

A system is provided having a generally sealed cabinet and separator. A blower is provided in the sealed cabinet to provide a negative pressure within the cabinet. A waste entrance is provided in the cabinet which provides a sealed, rotatable input for the introduction of hospital waste to the system. In the system, the input rotates upon operation of a switch to direct solid waste to a disintegrator, such as a hammermill, wiht a flow of disinfectant fluid. Upon disintegration, the waste particles and disinfectant fluid are carried to the separator which is sealed with the cabinet. The solid waste is separated from the decontaminant fluid which is then directed to a public sewer.

12 Claims, 6 Drawing Figures

HOSPITAL WASTE DISPOSAL SYSTEM

BACKGROUND OF THE INVENTION

This invention relates to a system for disposing of infectious hospital waste and, more particularly, to an aseptic system for disintegrating and disinfecting solid hospital waste including such items as hypodermic syringes, glassware, slides, and other such potentially hazardous materials.

U.S. Pat. No. 3,926,379 discloses a syringe disintegrator which preceded the system of this invention. The syringe disintegrator of this prior patent was noisy, unreliable, and unsuitable for use in the hospital areas where it was needed. Operation of the hammermill resulted in a potentially bacteria-laden exhaust from the apparatus, and the vibration of the cabinet on which the hammermill was mounted generated high levels of noise. Furthermore, the syringe disintegrator deposited the waste materials in a bag having a plurality of holes supported within a liquid container for disinfectant. The system required removal of the bag by hand and required periodic service of the system to both replace the disinfectant and to remove fragments of hospital waste from the disinfectant container.

SUMMARY OF THE INVENTION

In this invention, a system is provided having a generally sealed cabinet and separator. A blower is provided in the sealed cabinet to provide a negative pressure to the sealed system circuit in which the waste articles, waste particulate and disinfectant solution are channelled. A waste entrance is provided in the cabinet which provides a sealed, rotatable input for the introduction of hospital waste to the system. In the system, the input rotates upon operation of a switch to direct solid waste to a disintegrator, such as a hammermill, with a flow of disinfectant fluid. Upon disintegration, the waste particles and disinfectant fluid are carried to the separator which is sealed with the cabinet. The solid waste is separated from the decontaminant fluid which is then directed to a public sewer.

The waste entrance includes a concave tray rotatably coupled to a downwardly extending channel which is connected to the hammermill. A flexible sealing interface between the concave tray and the downwardly extending channel permits the maintenance of a negative pressure within the cabinet and isolates the cabinet and waste entrance from any vibration from the hammermill. The hammermill itself is carried on a rigid structural framework within the cabinet. The rigid structural framework is bolted directly to the floor through vibration-damping mountings with the cabinet trapped between the vibration-damping material of the mountings and the floor, thus isolating the cabinet from any vibrations of the hammermill.

The hammermill includes a rotating shaft that carries a plurality of hammer components and is supported by a pair of sealed bearings. The sealed bearings are carried by a pair of bearing supports that are carried by the hammermill housing. Each bearing support is provided with a drain opening located adjacent the bearings and with a conduit leading to the separator. The sealed bearings are thus protected from disinfectant solution that might otherwise be urged into the bearings in the operation of the hammermill.

The hammermill includes a trap door in one of its lower quadrants through which the hammer components can expel large waste particles. The hammermill trap door is open when the waste entrance is open for the input of waste. The trap door closes for a time period as a waste entrance tray begins its delivery of waste to the hammermill.

A separator, or external waste-collection system, includes a tank that forms the means to separate the solid waste from the disinfectant solution. The tank includes a series of partitions to form one or more collecting pools and a skim-prevention portion adjacent the output of the waste-removal system. A foraminous trap is provided between the collecting pools and the output of the waste-removal system which leads to a sewer.

In operation of the system of this invention, solid, infectious waste may be introduced into the system through the waste entrance. A flow of disinfectant solution is formed and mixed with the waste. The solid waste is reduced to particulate form in the presence of the disinfectant. The solid particulate waste is then separated from the disinfectant solution by introducing a flow of the particulate waste and disinfectant fluid to a collection pool and settling large particulate waste by gravity from the disinfectant. A flow may be provided from the surface of a first collection pool to a second collection pool to provide additional settling of smaller particulate waste. Flow is urged from the bottom of the second pool to trap floating particulate waste in the collection pool; and this flow, from the bottom of the collection pool, is directed upwardly over a weir portion and through a foraminous trap as a final collection of solid particulate waste prior to delivery of the disinfectant solution to the sewer.

The invention provides an aseptic hospital waste disposal system which is reliable and quiet and can be used in the patient wards of a hospital without the constant attention of hospital personnel.

Further features and advantages of the invention will be apparent from the following drawings and descriptions in which:

DETAILED DESCRIPTION OF THE PREFERRED EMBODIMENTS

Figure 1:
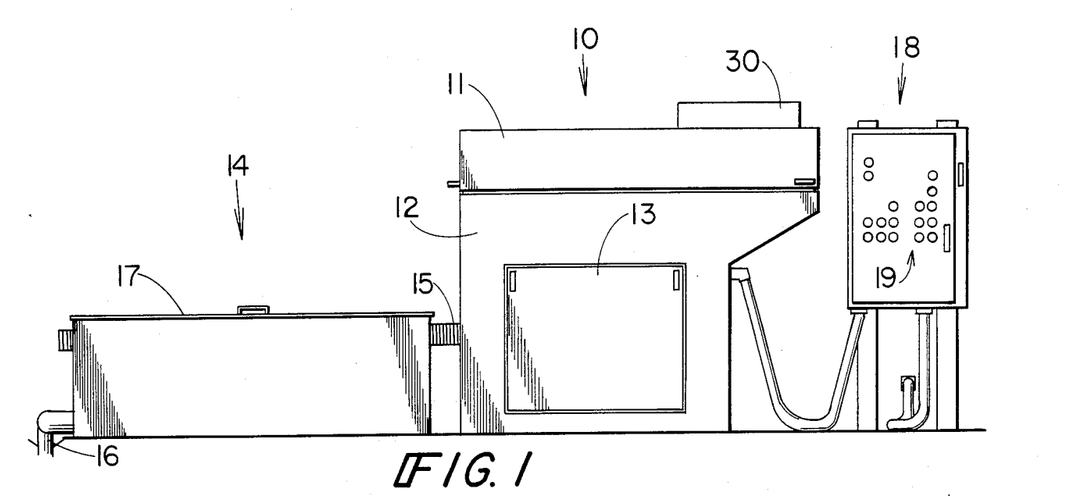
FIG. 1 is a plan view of system of the invention.

Referring now to the drawings, FIG. 1 shows the system of the invention including a generally sealed cabinet 10, a generally closed separator 14, and a system control 18. The generally sealed cabinet 10 provides an entrance for the input of waste to the system and houses a source of disinfectant solution; a disintegrator for solid waste (for example, a hammermill); a blower to provide a negative pressure from within the cabinet to the overall waste particulate-solution circuit; and electrical and hydraulic components to operate the waste entrance, the disinfectant source, and the hammermill. The cabinet 10 is provided with a hinged top 11 and a bottom 12 with a lockable door 13. The hinged top 11 and door 13 permit the components within the cabinet 10 to be conveniently serviced. The generally closed separator 14 is connected with the cabinet 10, communicates with the disintegrator through conduit 15, and is arranged to separate solid waste from the disinfectant solution and deliver the disinfectant solution to a public sewer 16. The separator 14 also includes a hinged top 17 to permit the disinfected solid waste to be periodically removed from the separator and placed in sealed bags for disposal in sanitary landfills. The system control 18 provides an electrical control circuit including a plurality of relays which permit the system to be operated by hospital personnel through predetermined sequences by a plurality of push-buttons 19.

Figure 2:
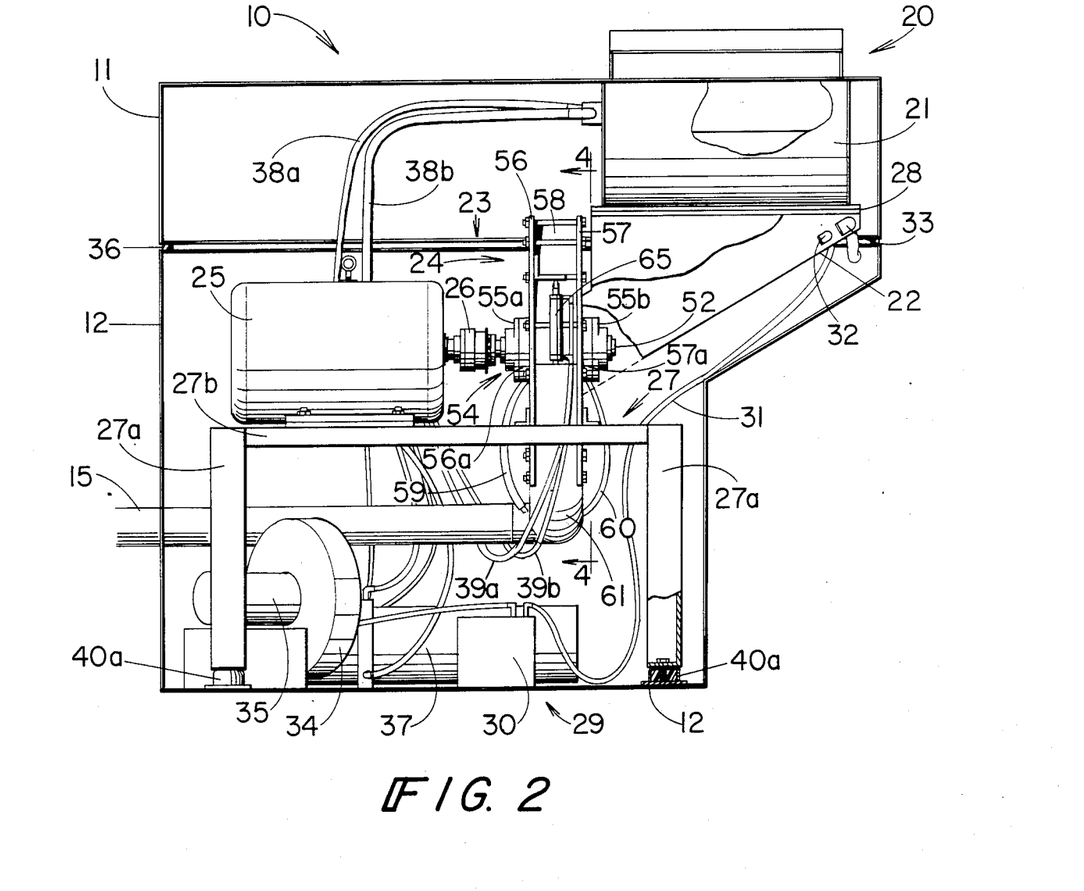
FIG. 2 is a view of the interior of the sealed cabinet into which the hospital waste is introduced for disintegration.

FIG. 2 is a view of the interior of the cabinet 10 as if the front face of cabinet 10 has been removed. The arrangement of system components within the sealed cabinet 10 is shown in FIG. 2. Such components include the waste entrance 20, the disintegrator 23 and its supporting structure 27, the disinfectant source 29, the source of negative pressure 34, and a hydraulic power source 37. As shown in FIG. 2, the waste entrance 20 is carried by the hinged top 11 of the cabinet 10. The waste entrance 20 extends downwardly through a closed conduit 21 (partially broken away) that opens into a downwardly extending chute 22 (also partially broken away) leading to the disintegrator system 23. The disintegrator system 23 includes a hammermill 24 driven by an electric motor 25 through a coupling 26. In large systems having a capacity of, for example, 0.65 cubic feet per load, a fifty-horse-power, three-phase motor is used to drive the hammermill. Such a motor is coupled to the hammermill with a torque-limiting coupling to prevent the motor from being stalled in the event of a jammed hammermill. The hammermill 24 and motor 25 are securely mounted to a rigid structural framework 27.

The interface between the conduit 21 leading from the waste entrance and the downwardly extending chute 22 is sealed by a flexible interface 28. The flexible interface 28 provides a pressurizing seal between the waste input 20 supported by the cabinet 10 and the downwardly extending chute 22 leading to the hammermill 24 and also isolates any slight vibration of the downwardly extending chute 22 that may occur in operation of the hammermill 24 from being transmitted to the waste input 20 and cabinet 10.

The cabinet 10 also includes a source of disinfectant 29 including a container 30 and an electrically driven pump (not shown) to deliver a flow of disinfectant through hose 31 to the interior of the downwardly extending chute 22. The interior of the downwardly extending chute is provided with means 32 to introduce the disinfectant and means 33 to introduce water, as shown in the partially broken view of chute 22. The pump in the source of disinfectant 29 and a valve (not shown) between means 33 and the hospital water system are operated by the system control 18 to provide a flow of water during operation of the system. As shown in FIG. 2 these means comprise two nozzles that are arranged to produce a disinfectant-water solution into which the hospital waste is delivered by the conduit 21. The mixed waste and disinfectant solution flow together down chute 22 to the interior of the hammermill 24. The waste entrance and disinfectant and water sources in combination thus provide a first means for providing a flow of water and a flow of disinfectant and for delivering solid waste and disinfectant solution to the hammermill. Within the hammermill, the waste is disintegrated into particulate form and further disinfected by the disinfectant solution. The particulate waste and disinfectant solution are then directed outwardly of the hammermill through conduit 61 and to the separator 14 through conduit 15.

Also contained within the cabinet 10 is a blower 34 driven by a motor 35. The blower 34 is driven in such a direction that it exhausts the air within the interior of cabinet 14 (through conduit 15) to a hospital ventilator leading outside of the hospital, and in so doing creates negative pressure on the waste particulate-solution circuitry ending in the waste separator means within separator housing 14. The cabinet 10 is provided with flexible seals 36, between the hinged top 11 and the bottom 12 of the cabinet and between door 13 and the bottom 12 of the cabinet 10 (not shown). The interior of cabinet 10 is thus provided with a negative pressure creating means 34 towards preventing aerosols that may be created in the operation of the hammermill from escaping the waste entrance and openings of cabinet 14. The cabinet 10 preferably includes a bacterial filter in the exhaust to prevent bacteria from being carried from the cabinet with the exhaust of blower 34.

An electrically powered hydraulic pump or pressure source 37 is provided within cabinet 10 to actuate hydraulic components, such as hydraulic cylinders, and to operate movable components of the waste entrance 20 and hammermill 24 through hydraulic hoses 38a and 38b and 39a and 39b.

The structural framework 27 for the disintegrator system 23 may be constructed by welding together U-shaped and L-shaped iron rods to provide four legs 27a and transverse beams 27b to position and support the disintegrator components within the cabinet 10. The legs 27a of the supporting structure 27 for the disintegrator 23 are bolted directly to the hospital floor through vibration-damping mountings 40 with the bottom 12 of the cabinet 10 being trapped between the vibration-damping material 40a of mountings 40 and the hospital floor (see FIG. 4).

Figure 3:
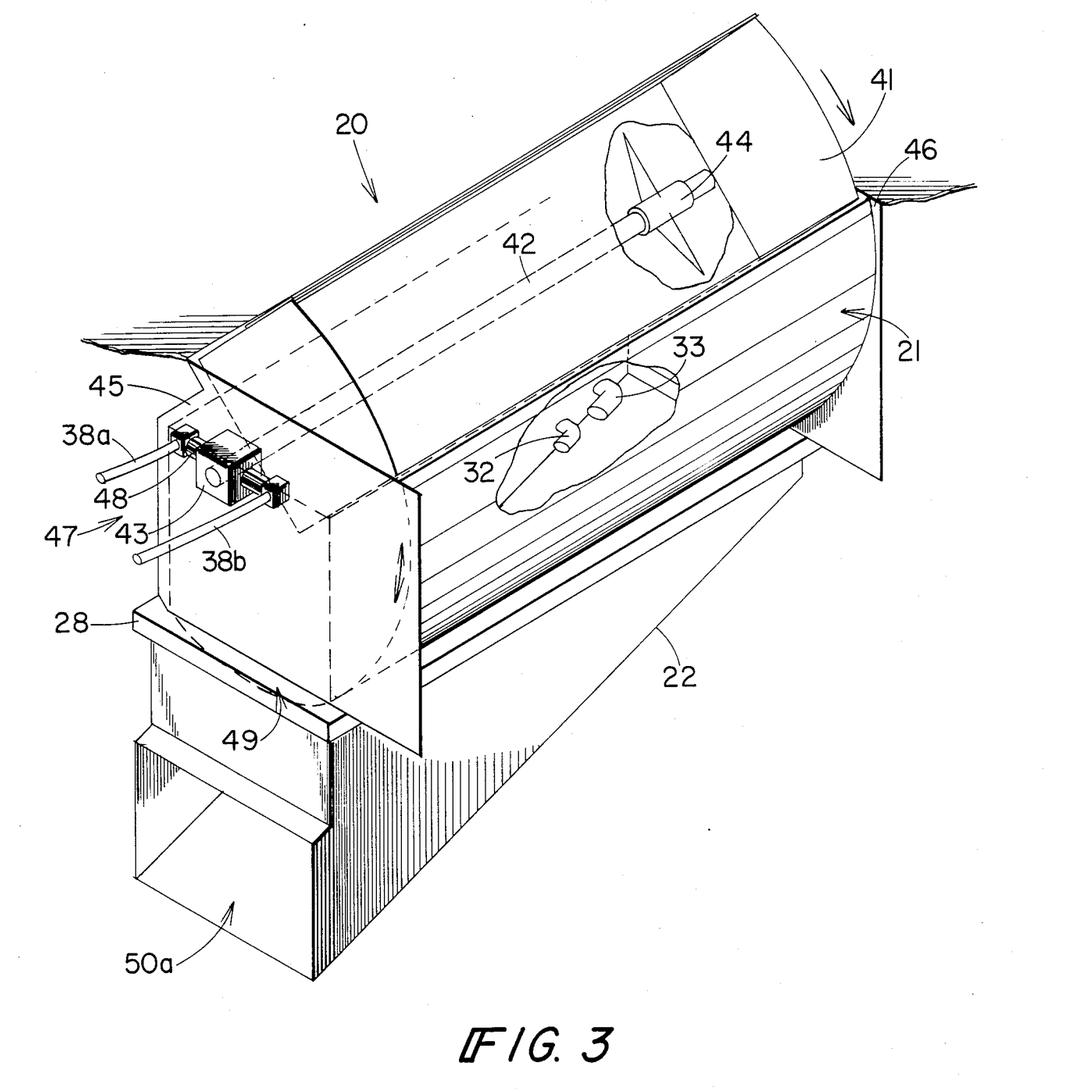
FIG. 3 is a partially broken-away, perspective view of the waste entrance of the system.

The waste entrance is shown in greater detail in the partially broken-away perspective view of FIG. 3. As shown in FIG. 3, the waste entrance 20 provides a movable and generally sealed waste input and includes a concave tray 41 which is carried on a rotating shaft 42 (shown in phantom lines) journalled into end frames 43 and 44 carried by the side panels 45 and 46 of the structure forming conduit 21. The concave tray is generally U-shaped and may be rotated about the generally horizontal axis of shaft 42. The U-shaped tray 41 is driven about the generally horizontal axis by a hydraulic cylinder operated rotary actuator and lever arrangement 47, the hydraulic actuator 48 being connected with the hydraulic power source 37 through hydraulic hoses 38a and 38b. The U-shaped tray 41 has a first position which is upwardly open, as shown in FIG. 3, to permit hospital waste to be inserted into the system. The waste entrance 20 is operated by a switch (not shown) which begins a sequencing of relays within system control 18 (FIG. 1) to operate the valves in the hydraulic system 37 and drive the hydraulic cylinder 48, rotating the U-shaped tray from its first position to a second downward position 49, shown in phantom lines in FIG. 3. The system control 18 permits operation of the pump in the source of disinfectant 37 (FIG. 2) to deliver a flow of disinfectant to the interior of the downwardly extending channel 22 through the nozzle 32, and operation of the water valve to permit water to flow from nozzle 33, thus mixing of disinfectant with the solid waste prior to its delivery to the hammermill through opening 50a. As shown in greater detail in FIG. 3, the sealing interface 28 is positioned between the waste input 20 and the downwardly extending channel 22 to seal and to isolate mechanically these two portions of the system from each other. The sealing interface may be a closed pore elastomeric compound such as Neoprene to prevent the accumulation of infectious material.

Figure 4:
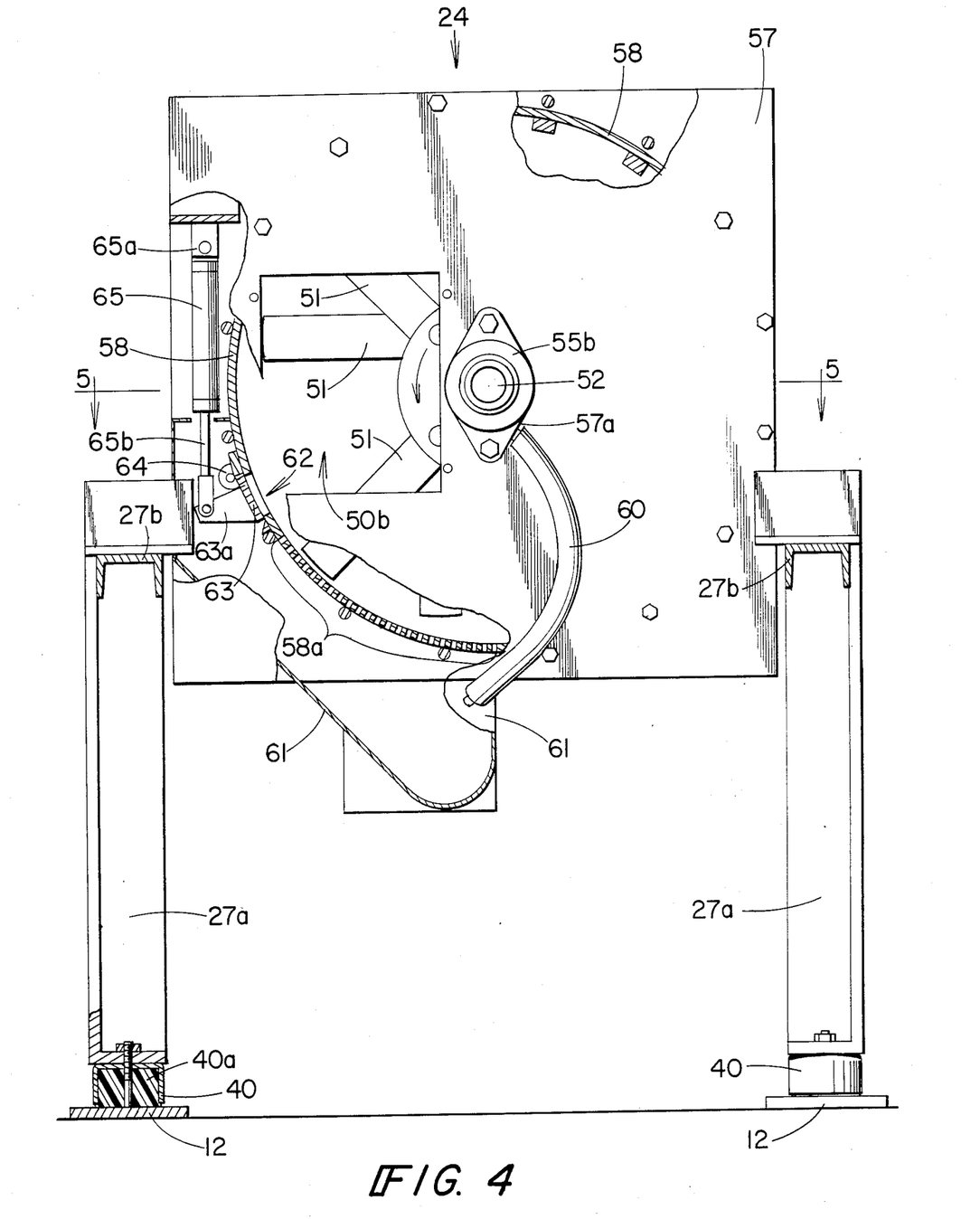
FIG. 4 is a partial, cross-sectional view of the hammermill and its supporting structure taken along lines 4—4 of FIG. 2.
Figure 5:
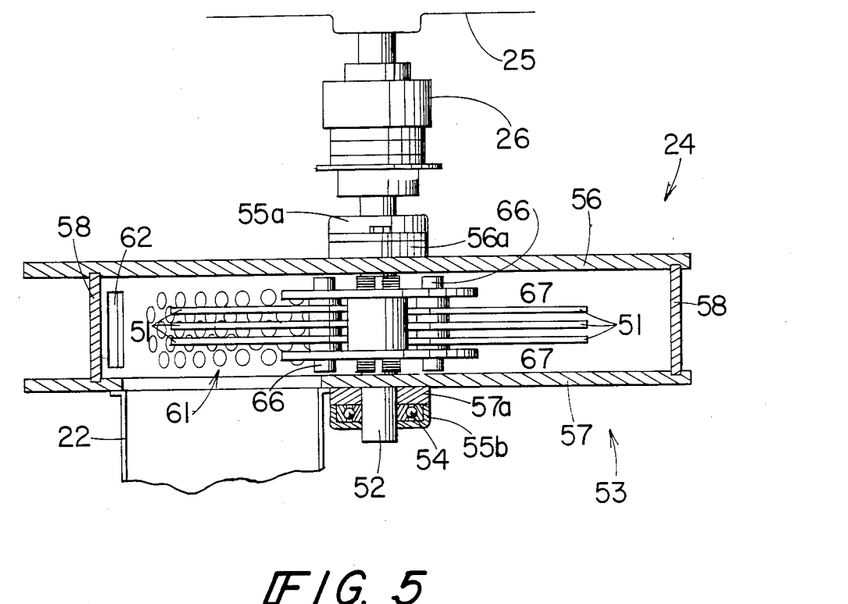
FIG. 5 is a cross-sectional view of the hammermill taken along lines 5—5 of FIG. 4.

The hammermill 24 is shown in greater detail in FIG. 4 and FIG. 5. The hammermill is formed by a plurality of hammer components 51 hingedly carried about a rotating shaft 52 within a housing 53. As more specifically shown and described with respect to FIG. 5, the rotating shaft and hammer components are supported by a pair of sealed bearings 54 which are themselves carried by a pair of bearing supports 55a and 55b carried by the hammermill housing 53. The hammermill housing 53 itself comprises a pair of side frames 56 and 57 bolted together about a peripheral casing 58. Each of the side casings 56 and 57 carries an extended support, respectively 56a and 57a, upon which bearing supports 55a and 55b, respectively, are mounted. The supports 56a and 56b are short, cylindrical structures fastened to and sealed with the housing sides 56 and 57. Supports 56a and 56b are provided with openings adjacent each of the bearings 54 which are connected through conduits 59 and 60 (FIG. 2) with the conduit 61 leading from the hammermill 24 to a separator 14.

Downwardly extending chute 22 may be fastened to and sealed with side casing 57 of the hammermill at their openings 50a and 50b. Hospital waste and disinfectant travelling down chute 22 enter opening 50b in hammermill side plate 57, as shown in FIG. 4. Side plate 57 of FIG. 4 is partially broken away to show the hammer components 51 (see also FIG. 5), the arrangement of openings 58a in the lower quadrants of the peripheral casing member 58, and the trap door opening 62. The opening 62 is closed by a trap door 63 supported by hinges 64 from the peripheral casing 58. A hydraulic cylinder 65 is also carried by the hammermill housing at one end 65a, and its piston 65b is connected with a flange 63a of the trap door 63. Waste and disinfectant entering opening 61 are disintegrated by the hammermill 24 (which rotates counterclockwise as shown in FIG. 4). The solid hospital waste is broken apart and further mixed with disinfectant by the rotating hammermill components 51 within the chamber 66 defined by the housing 53 formed by plates 56 and 57 and peripheral casing member 58 until it is reduced to sufficient size to be thrown through openings 58a and into discharge conduit 61.

The rotating hammer assembly is shown in greater detail in FIG. 5 which is a cross-sectional view of FIG. 4 taken along lines 5—5 of FIG. 4. The rotating hammer assembly includes a plurality of rod-like hammer elements 51 which are carried by and are freely rotatable on a plurality of pins 66. As many as twelve hammer elements 51 are carried on four pins securely fastened between a pair of supporting spider elements 67 that are fixed to the rotating shaft 52. The hammer elements 51 may be steel rods one to three inches by one-fourth to one-half inch in cross section and three to twelve inches long that are carried on pins one-half to one inch in diameter depending upon machine capacity. During rotation of the hammermill, at high speeds, for example, on the order of 3500 rpm, the hammer components 51 strike the solid waste, breaking it into pieces within a chamber. After the flailing hammer elements 51 have continued to strike and break the solid waste, it is reduced to a size sufficient to pass through the openings 58a.

In the operation of the hammermill 24, disinfectant introduced into the hammermill with the solid waste can be forced through the seals in bearings 54 where it washes away the lubrication for the ball bearing, leading to early failure of the hammermill. As previously indicated with respect to FIGS. 4 and 5, the hammermill housing plates 56 and 57 carry extended support portions 56a and 57a which are provided with drain openings 56b and 57b. Referring specifically to FIG. 5, the hammermill support extension 57a adjacent bearing support 55b illustrates the placement of drain opening 57b adjacent bearing 54. Opening 57b prevents disinfectant from being forced into the bearing 54. Disinfectant is drained through opening 57b from adjacent the bearing 54 through tubular conduit 60 (FIG. 4) into the discharge conduit 61. The bearing support portion 56a of hammermill housing plate 56a is similarly provided with an opening (not shown) and conduit 59 (FIG. 2).

In order to clear the hammermill of any large solid elements which have not been sufficiently reduced in size to pass through the openings 58a when an additional load of waste material is placed in the system, the system control 18 operates the hydraulic piston actuator 65 simultaneously with rotation of the movable input 41 to deliver waste material into the system. System control 18 operates the trap door actuator 65 to close the trap door for a typical interval of two to three seconds following operation of the waste entrance so that the new load of waste and disinfectant is trapped in the hammermill until it is reduced to sufficient size to pass through the openings 58a. The system control 18, through hydraulic actuator 65, reopens the trap door 63 in the lower quadrant of peripheral casing 58 after a predetermined time of operation so that waste material too large to pass through openings 58a will be expelled through the large opening 62 in the peripheral casing 58 and into discharge chute 61 by the rotating hammer elements 51.

Figure 6:
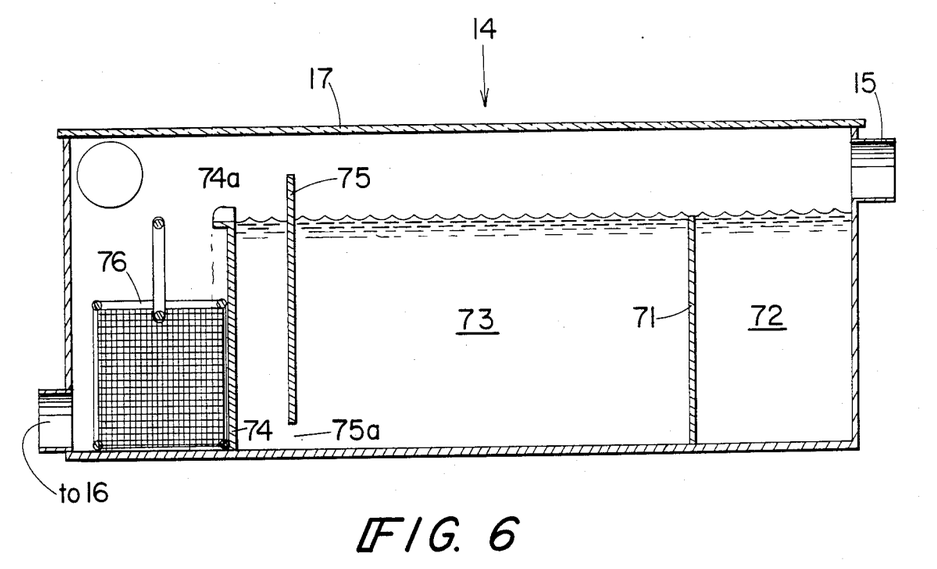
FIG. 6 is a cross-sectional view taken longitudinally through the center of the separator of the system.

As shown in FIGS. 1, 2, and 6, hospital waste and disinfectant travel through the waste discharge conduits 61 and 15 into the separator 14, shown in the cross-sectional view of FIG. 6. The separator 14 includes a plurality of partitions to separate the solid waste and disinfectant solution. One partition forms first weir 71 forming a first collecting pool 72 for the collection of solid waste from the disinfectant solution by gravity. Disinfectant solution and those portions of solid hospital waste light enough to escape the first collection pool 72 flow over the first weir 71 into a second collection pool 73 formed by a second weir-forming partition 74. Additional settling of hospital waste through the effect of gravity occurs in the second pool 73. Furthermore, floating waste is trapped by a further partition 75 in the second pool 73. Partition 75 is supported within the separator above its bottom to define an opening 75a adjacent the bottom of the second pool 73. As a result of this arrangement, disinfectant solution is drawn from the bottom of the second pool 73 and flows over weir portion 74a, thus largely trapping any remaining solid waste in the second pool 73. In order to further ensure that solid waste is not delivered from the separator into the public sewer, flow over the weir portion 74a is directed into a foraminous container 76 as a final trap for solid waste. The disinfectant solution flows through the openings in the foraminous container 76 and outwardly from the separator into the public sewer.

The waste disposal system of this invention thus provides an aseptic method of disposal of hospital waste. In this method, solid hospital waste is introduced into a disintegrator with a flow of disinfectant solution. The solid waste is reduced to particulate form in the presence of the decontaminant and separated from the decontaminant, which is discharged in the absence of solid waste into a public sewer.

A flow of solid particulate waste and disinfectant solution is directed to a separator forming a collection pool, and large particulate matter is settled by gravity from the disinfectant solution. The disinfectant solution can be directed to flow from a first pool to a second pool to provide additional settling of any particulate waste carried by this flow. Decontaminant waste is allowed to flow only from the bottom of the collection pool to trap floating waste in the collection pool, and this flow is directed upwardly over a weir and through a foraminous trap to collect any remaining solid particulate material before the decontaminant is directed into a public drain.

The system can thus handle large volumes of solid waste. The system requires only occasional attention to remove the solid waste collected in the separator 14. Hospital waste is thus reliably disinfected and reduced into small pieces which can be safely handled by hospital personnel. In addition, the flow of decontaminant into the hospital drain beneficially reduces the bacteria that may otherwise be present in the drain.

Although a specific embodiment of this system is shown and described, other embodiments and arrangements may be devised using the subject matter of this invention without departing from the scope of the following claims.

We claim:

1. A waste disposal system for treating and disposing of infectious waste articles in a substantially controlled closed and sealed aseptic circuit and for converting said infectious waste articles into a safely disposable noninfectious and non-toxic residue through the thorough disintegration and disinfection of such articles, said system comprising:

waste article feeding means for transferring said waste articles to waste article delivery means operably attached thereto, disintegrator means operably positioned to receive said waste articles from said waste article delivery means for disintegrating said waste articles into substantially small waste particulate for further treatment and disposal of same by said waste disposal system;

said disintegrator means comprising a rotary hammermill for violently disintegrating said waste articles at a substantially high speed, into a waste particulate-disinfectant solution:

said rotary hammermill means being powered by hammermill motor means operably coupled thereto;

disinfectant spray means operably positioned adjacent one or more of said waste article feeding means, said waste article delivery means and said disintegrator means for enveloping and impregnating said waste articles and said waste particulate in a bacteria killing disinfecting liquid solution, liquid-solid particle separation means operably attached to said disintegrator means for separating, on a substantially continuous basis, said disintegrated particles of solid waste from said enveloping and impregnating disinfectant liquid;

said liquid-solid particle separation means including operable connections to liquid evacuation means and solid particulate evacuation means for continuous disposal of said disinfectant liquid and batch disposal of said solid waste particulate respectively; and system vacuum means operably associated with said disposal system for creating a negative pressure within said system for effectively precluding the inadvertent release of bacteria and other contamination during the treatment and disposal of said waste articles by said system;

said system vacuum means cooperating with said liquid-solid particle separation means to exhaust any such bacteria or contaminant laden air emanating thereinto from said rotary hammermill means to in turn, exert a negative pressure on the substantially closed and sealed circuit created by said waste article feeding means, said waste article delivery means, and said disintegrator means leading into said liquid-solid particle separation means.

2. The waste disposal system of claim 1 in which the invention further comprises system cabinet means operably disposed about said waste article feeding means, said waste article delivery means, said disintegrator means, said rotary hammermill means and said disinfectant spray means for maintenance of same in operably respective attachment therewithin, all in a substantially sealed housing environment.

3. The waste disposal system according to claim 2 in which said invention further comprises liquid-solid particle separation cabinet means operably and sealingly disposed about said liquid-solid particle separation means, said liquid-solid particle separation cabinet means being operably attached to said system cabinet means for the acceptance of waste article particulate and disinfectant solution from said system cabinet means into said liquid-solid separation means within said liquid-solid particle separation cabinet.

4. The invention according to claim 1 in which said waste article feeding means comprises a waste article feed apparatus capable of accepting waste articles, for processing by said waste disposable system, from a first open position to enable the inputing of said hospital waste to a second closed position, said waste article feeding means maintaining in a substantially sealed environment the substantially closed and sealed circuit created by said waste article feeding means, said waste article delivery means and said disintegrator means, regardless of whether said waste article feeding means is in either said first open or in said second closed positions, said waste article feeding means serving to continuously seal said closed and sealed system circuit to prevent the inadvertent release of bacteria laden atmosphere and waste article particles from out of said system circuit at said waste article feeding means location.

5. The invention according to claim 4 in which said waste article feeding means comprises a concave tray assembly rotatably coupled to said waste article delivery means through a flexible, continously sealing interface,
   said concave tray apparatus being rotatable from a first open position to enable said inputting of said hospital waste to a second closed position,
   said concave tray assembly remaining in said sealed engagement relative to said system circuit while in both said first open and second closed positions.

6. The invention according to claim 1 in which said waste article delivery means comprises a substantially sealed conduit delivery member operably interposed and sealed between said waste article feeding means and said rotary hammermill means,
   said disinfectant spray means being operably attached along said conduit delivery member for delivery of said disinfecting liquid solution about said waste articles passing therethrough said waste article delivery means,
   said conduit delivery member including one or more disinfecting solution nozzles for introduction of one or more of said disinfecting liquid solution and water into said conduit delivery member,
   said one or more nozzles being arranged to mix one or more of said disinfectant liquid solution and water together and with said waste article for delivery of same to said rotary hammermill for disintegration of said disinfectant impregnated and enveloped waste article therewithin.

7. The invention according to claim 1 in which said disintegrator means includes said rotary hammermill operably positioned with rotary hammermill housing means,
   said rotary hammermill housing means being operably attached in sealed relationship to both said waste article delivery means and said liquid-solid particle separation means respectively,
   said rotary hammermill further including a plurality of bearing supports with sealed bearings for cooperation with a rotating hammermill shaft, one or more of said plurality of bearing supports having an opening located adjacent said respective sealed bearings to permit the removal of accumulated waste particles and disinfectant solution from said sealed bearings as required.

8. The invention according to claim 7 in which said rotary hammermill housing is carried and supported by a structural framework that includes vibration dampening mounting elements adapted to be secured to a floor.

9. The invention according to claim 8 in which said rotary hammermill housing means is possessed of outer surfaces covered by a sound-absorbing material,
   said rotary hammermill housing having a side entry aperture and bottom exit apertures, said side entry aperture operably and sealingly attached to said waste article delivery means and said bottom exit apertures operably and sealingly attached to said liquid-solid particle separation means, through respective flexible sealing members, for isolating the vibration created by said disintegrator means from the remainder of said waste disposal system.

10. The waste disposal system according to claim 1 in which the invention further comprises disinfectant solution storage means operably attached to said disinfectant spray means for supplying said disinfecting liquid solution to said system.

11. The invention according to claim 1 in which said liquid-solid particle separation means comprises a liquid-solid separator member having an arrangement of weirs to separate solid waste particulate transmitted by said rotary hammermill, from the disinfectant solution accompanying same, said arrangements of weirs forming at least one collecting pool and a skim prevention portion,
   said liquid-solid separator apparatus further including a foraminous trap between said skim prevention portion and said solid particle evacuation means to trap a portion of said solid waste particulate prior to the transmission of said separated disinfectant solution to said sewer connection member.

12. The invention according to claim 1 in which said system vacuum means comprises blower means operably positioned to exhaust atmosphere proximate to said liquid-solid particulate separation means for the controlled and direct release of said exhaust from said system,
   said blower means further including a bacteria filter for substantial removal of bacteria and other contaminants from the atmosphere immediately proximate to said liquid-solid particle separation means.

* * * * *

UNITED STATES PATENT AND TRADEMARK OFFICE
CERTIFICATE OF CORRECTION

PATENT NO. : 4,618,103
DATED : October 21, 1986
INVENTOR(S) : Joseph H. Wilson; David N. Lasiter; Randall G. McKee It is certified that error appears in the above-identified patent and that said Letters Patent is hereby corrected as shown below:

In the ABSTRACT, line 8      "wiht" should be instead -- with --

Col. 7, line 62      after "solution", ":" should be instead -- , --

Signed and Sealed this

Fourteenth Day of April, 1987

Attest:

DONALD J. QUIGG

Attesting Officer      Commissioner of Patents and Trademarks